US010702865B2

(12) United States Patent
Kazumura et al.

(10) Patent No.: US 10,702,865 B2
(45) Date of Patent: Jul. 7, 2020

(54) MEASUREMENT CONTAINER

(71) Applicant: HAMAMATSU PHOTONICS K.K., Hamamatsu-shi, Shizuoka (JP)

(72) Inventors: Kimiko Kazumura, Hamamatsu (JP); Hiroshi Tsuchiya, Hamamatsu (JP)

(73) Assignee: HAMAMATSU PHOTONICS K.K., Hamamatsu-shi, Shizuoka (JP)

( * ) Notice: Subject to any disclaimer, the term of this patent is extended or adjusted under 35 U.S.C. 154(b) by 233 days.

(21) Appl. No.: 15/672,509

(22) Filed: Aug. 9, 2017

(65) Prior Publication Data
US 2018/0043353 A1 Feb. 15, 2018

(30) Foreign Application Priority Data

Aug. 10, 2016 (JP) .................................. 2016-157799

(51) Int. Cl.
*B01L 3/00* (2006.01)
*G01N 33/52* (2006.01)
(Continued)

(52) U.S. Cl.
CPC ............... *B01L 3/502* (2013.01); *G01N 21/03* (2013.01); *G01N 33/52* (2013.01);
(Continued)

(58) Field of Classification Search
CPC ........ G01N 33/49; G01N 21/76; G01N 15/14; G01N 15/12; G01N 21/03; G01N 21/645;
(Continued)

(56) References Cited

U.S. PATENT DOCUMENTS

2004/0180346 A1\* 9/2004 Anderson ............ C12Q 1/6806
435/6.18
2006/0002804 A1\* 1/2006 Jiang ................... B01F 13/0059
417/410.1
2015/0010995 A1\* 1/2015 Shin ................... G01N 33/4905
435/288.7

FOREIGN PATENT DOCUMENTS

JP 2006-043607 A 2/2006
JP 2006-053091 A 2/2006
(Continued)

OTHER PUBLICATIONS

Agarwal et al. "Programmable Autonomous Micromixers and Micropumps" Journal of Microelectromechanical Systems, 14, 6, 2005 (Year: 2005).\*
(Continued)

*Primary Examiner* — Samuel P Siefke
*Assistant Examiner* — Quocan B Vo
(74) *Attorney, Agent, or Firm* — Faegre Drinker Biddle & Reath LLP

(57) ABSTRACT

Provided is a measurement container including a container body where a first region, a second region, and an intermediate region are continuously formed as an accommodation space accommodating a sample and an inlet is formed and a rotor which is arranged in the second region and rotated by an effect of magnetic force. The container body includes a wall portion which defines the accommodation space and at least a portion of which has a light transmitting property and a partitioning portion which partitions the intermediate region into one side and the other side in a second direction perpendicular to the first direction. The partitioning portion partitions the intermediate region into the one side and the other side so that a communication region which allows the one side and the other side to communicate with each other in the intermediate region remains.

8 Claims, 9 Drawing Sheets

(51) Int. Cl.
  *G01N 21/03* (2006.01)
  *G01N 21/64* (2006.01)
  *G01N 21/76* (2006.01)

(52) U.S. Cl.
  CPC . *B01L 2300/088* (2013.01); *B01L 2300/0809* (2013.01); *B01L 2300/0848* (2013.01); *B01L 2400/043* (2013.01); *G01N 21/645* (2013.01); *G01N 21/76* (2013.01); *G01N 2021/0346* (2013.01)

(58) Field of Classification Search
  CPC ... G01N 2001/248; G06F 19/00; B01L 3/502; B01L 2300/0809; B01L 2300/0848; B01L 2300/088; B01L 2400/043; B01L 3/50; B01L 3/00
  See application file for complete search history.

(56) References Cited

FOREIGN PATENT DOCUMENTS

| | | |
|---|---|---|
| JP | 5317988 B2 | 10/2013 |
| JP | 2014-526695 A | 10/2014 |
| WO | WO-2013/038127 A1 | 3/2013 |
| WO | WO2016122645 A1 * 8/2016 | ............. G01N 33/48 |

OTHER PUBLICATIONS

Kimura et al. "An integrated microfluidic system for long-term perfusion culture and on-line monitoring of intestinal tissue models", Royal Society of Chemistry Lab Chip, 2008, 8, 741-746 (Year: 2008).*

* cited by examiner

MEASUREMENT CONTAINER

TECHNICAL FIELD

The present disclosure relates to a measurement container accommodating a sample.

BACKGROUND

In order to measure characteristics of a sample by using light, there are cases where a measurement container accommodating the sample is used (for example, refer to Japanese Translation of PCT International Application Publication No. 2014-526695 and Japanese Patent No. 5317988).

SUMMARY

In the measurement container as described above, there are cases where a plurality of solutions are introduced as samples.

Therefore, an object of the present disclosure is to provide a measurement container capable of efficiently and uniformly mixing a plurality of solutions when the plurality of solutions are introduced.

A measurement container of the present disclosure is configured to include a container body where a first region and a second region located at both ends in a first direction and an intermediate region located between the first region and the second region are continuously formed as an accommodation space accommodating a sample and an inlet through which the sample is introduced into the accommodation space is formed and a rotor which is arranged in the second region and rotated by an effect of magnetic force, wherein the container body includes a wall portion which defines the accommodation space and at least a portion of which has a light transmitting property and a partitioning portion which partitions the intermediate region into one side and the other side in a second direction perpendicular to the first direction, and wherein the partitioning portion partitions the intermediate region into the one side and the other side so that a communication region which allows the one side and the other side to communicate with each other in the inter mediate region remains.

In this measurement container, the partitioning portion partitions the intermediate region into the one side and the other side, and the rotor is rotated by the effect of magnetic force in the second region. Therefore, when a plurality of solutions are introduced, the plurality of solutions are mixed while the plurality of solutions flow in a looping flow path from the first region sequentially through the one side of the intermediate region, the second region, and the other side of the intermediate region and returning to the first region. In addition, in this measurement container, the partitioning portion partitions the intermediate region into the one side and the other side so that a communication region which allows the one side and the other side to communicate with each other in the intermediate region remains. Accordingly, flowing of a plurality of solutions and mixing of a plurality of solutions are facilitated. Therefore, according to the measurement container, when a plurality of solutions are introduced, it is possible to efficiently and uniformly mix the plurality of solutions.

In the measurement container of the present disclosure, the container body may have a shape of a flat plate of which thickness direction is a third direction perpendicular to the first direction and the second direction. Accordingly, because the thickness (the thickness in the third direction) of the looping flow path is reduced, when a plurality of solutions are introduced, it is possible to more efficiently and more uniformly mix the plurality of solutions. In addition, because the thickness (the thickness in the third direction) of the accommodation space is reduced, it is possible to efficiently irradiate the sample accommodated in the accommodation space with light, and the influence of light absorption of a blood sample on the measurement accuracy is minimized, so that it is possible to efficiently collect the light emitted from the sample.

In the measurement container of the present disclosure, the wall portion may have a first wall portion and a second wall portion that face each other and are fixed to each other in a third direction perpendicular to the first direction and the second direction, and the accommodation space may include at least a space inside a recess portion formed in the first wall portion. Accordingly, it is possible to easily and reliably form the accommodation space in which the partitioning portion is arranged.

In the measurement container of the present disclosure, the wall portion may have a first inner surface and a second inner surface that face each other with the accommodation space interposed therebetween in a third direction perpendicular to the first direction and the second direction, and the partitioning portion may be provided on the first inner surface so that a gap as the communication region is formed between the first inner surface and the second inner surface. Accordingly, it is possible to easily and reliably form the partitioning portion which partitions the intermediate region while leaving the communication region.

In the measurement container of the present disclosure, the rotor may be rotated about an axis parallel to a third direction perpendicular to the first direction and the second direction, and the second region may have a shape corresponding to a rotation region of the rotor. Accordingly, it is possible to more efficiently flow the solution in the above-described looping flow path.

In the measurement container of the present disclosure, the rotor may be a rod-shaped member, the container body may further have a support portion which supports the rotor in the second region, and the surface of the support portion may have a curved surface shape that is convex toward the accommodation space. Accordingly, it is possible to rotate the rotor efficiently and stably, for example, by a magnetic stirrer.

In the measurement container of the present disclosure, the inlet may be opened to the first region. Accordingly, it is possible to suppress the restriction on the layout in comparison with a case where the inlet is opened to the second region or the intermediate region.

A measurement container of the present disclosure is configured to include a container body where a first region and a second region located at both ends in a first direction and an intermediate region located between the first region and the second region are continuously formed as an accommodation space accommodating a sample and an inlet through which the sample is introduced into the accommodation space is formed, wherein the container body includes a wall portion which defines the accommodation space and at least a portion of which has a light transmitting property and a partitioning portion which partitions the intermediate region into one side and the other side in a second direction perpendicular to the first direction, wherein the second region is a region where a rotor to be rotated by an effect of magnetic force is arranged, and wherein the partitioning portion partitions the intermediate region into the one side and the other side so that a communication region which allows the one side and the other side to communicate with each other in the intermediate region remains.

According to the measurement container, for the above-mentioned reasons, when a plurality of solutions are introduced, it is possible to efficiently and uniformly mix the plurality of solutions.

According to the present disclosure, it is possible to provide a measurement container that can mix a plurality of solutions efficiently and uniformly when the plurality of solutions are introduced.

DETAILED DESCRIPTION

Figure 1:
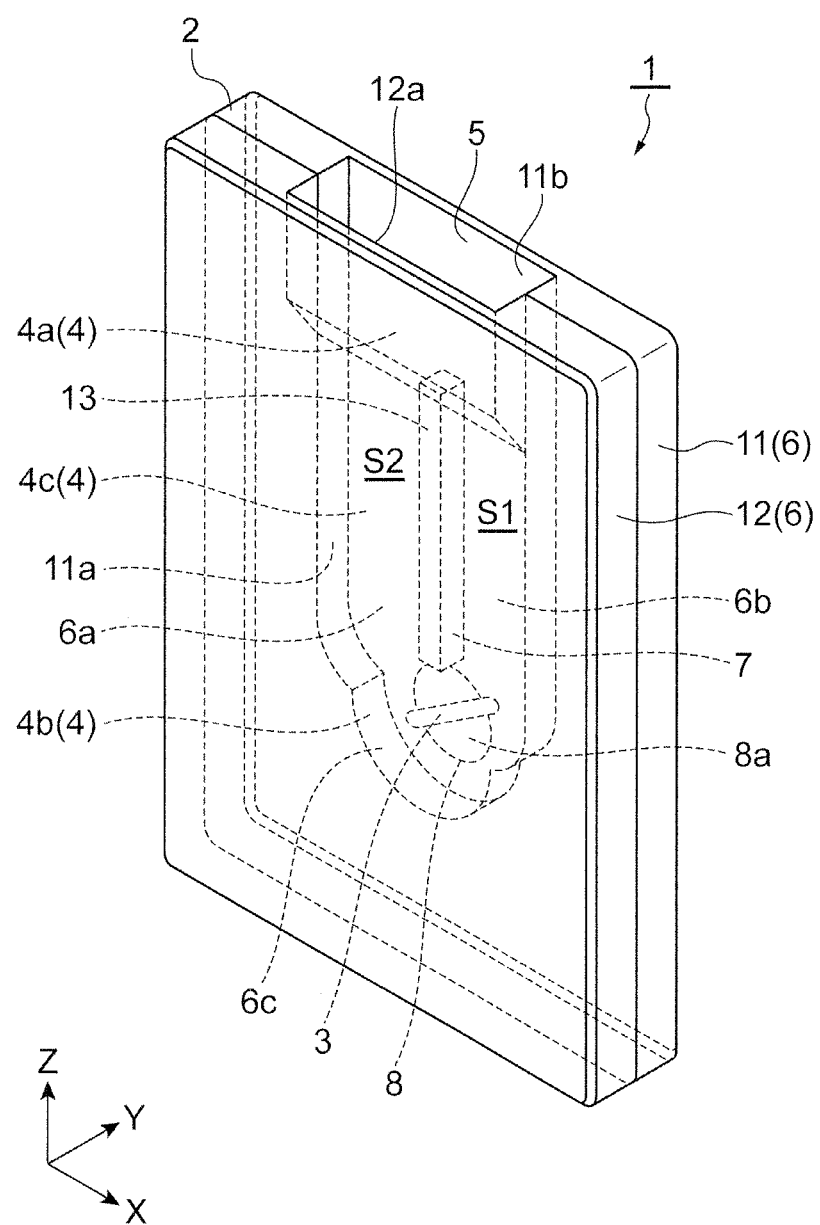
FIG. 1 is a perspective view of a measurement container according to an embodiment.
Figure 2:
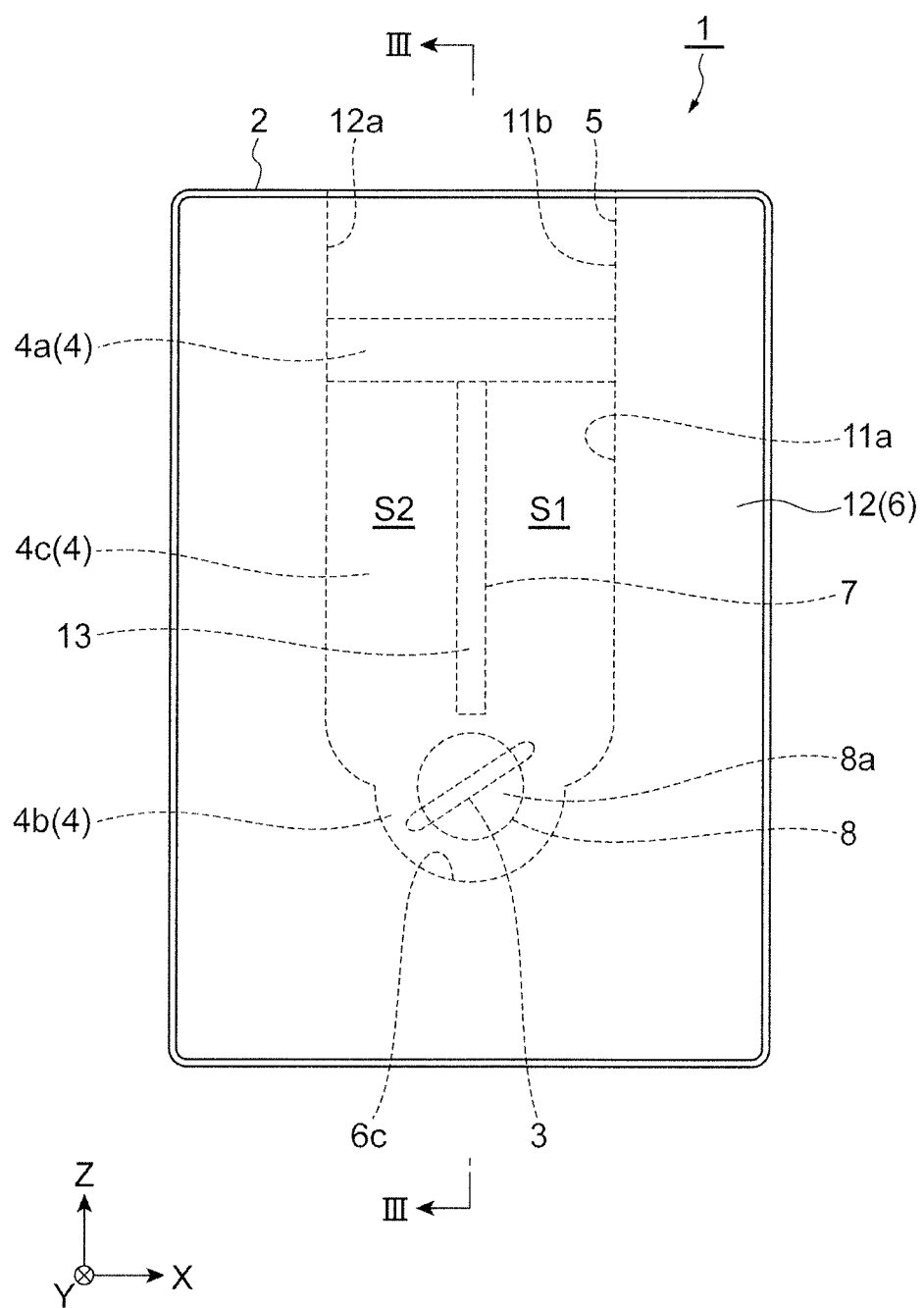
FIG. 2 is a front view of the measurement container of FIG. 1.
Figure 3:
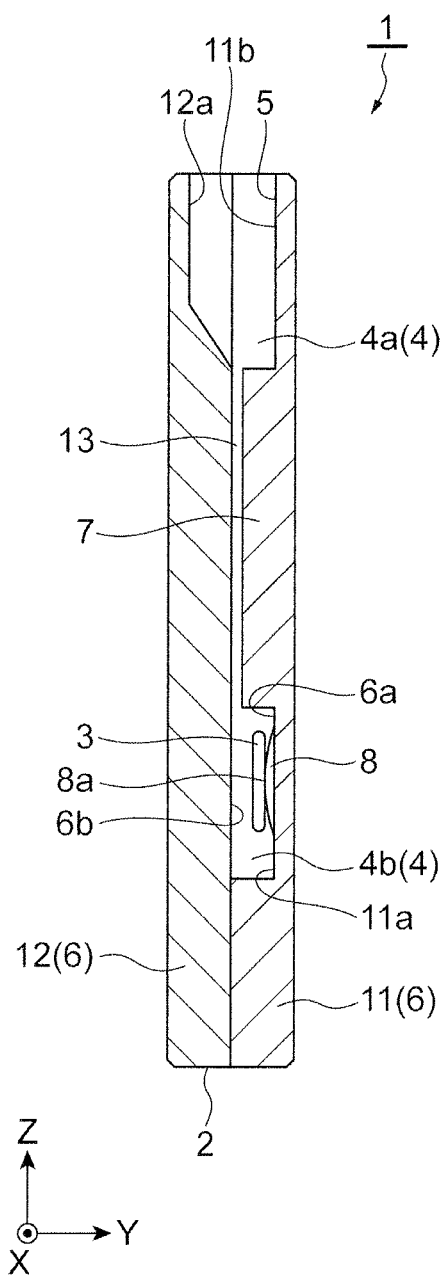
FIG. 3 is a cross-sectional view taken along line of FIG. 2.
Figure 4:
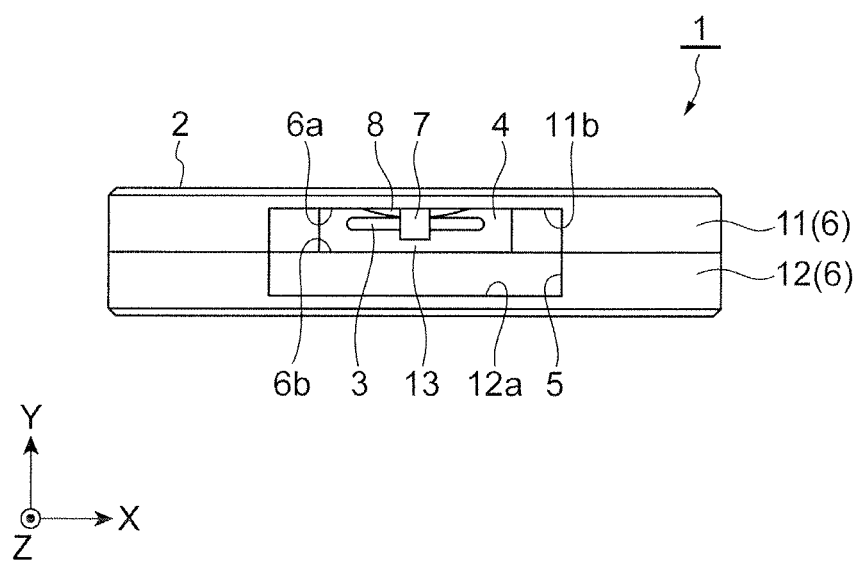
FIG. 4 is a plan view of the measurement container of FIG. 1.

Hereinafter, an embodiment of the present disclosure will be described in detail with reference to the drawings. In figures, the same or corresponding components are denoted by the same reference numerals, and redundant description thereof is omitted.

As illustrated in FIGS. 1 to 4, a measurement container 1 is configured to include a container body 2 and a rotor 3. In the container body 2, a first region 4a, a second region 4b, and an intermediate region 4c are continuously formed as an accommodation space 4 accommodating a sample. The first region 4a and the second region 4b are located at both ends of the accommodation space 4 in a Z-axis direction (first direction). The intermediate region 4c is located between the first region 4a and the second region 4b. In addition, an inlet 5 is formed in the container body 2. The inlet 5 is opened to the first region 4a. The introduction of the sample into the accommodation space 4 is performed from the inlet 5.

The container body 2 has a wall portion 6, a partitioning portion 7, and a support portion 8. The wall portion 6 defines the accommodation space 4. The wall portion 6 is formed of a material having a light transmitting property (for example, a transparent resin material), and thus, the entire wall portion 6 has a light transmitting property. The partitioning portion 7 partitions the intermediate region 4c into one side S1 and the other side S2 in an X-axis direction (a second direction perpendicular to the first direction). The partitioning portion 7 extends in the Z-axis direction and is formed integrally with the wall portion 6 by the same material as the wall portion 6. The support portion 8 supports the rotor 3 in the second region 4b.

The wall portion 6 has a first wall portion 11 and a second wall portion 12. The first wall portion 11 and the second wall portion 12 face each other in a Y-axis direction (a third direction perpendicular to the first direction and the second direction) and are fixed to each other. Each of the first wall portion 11 and the second wall portion 12 is formed in; for example, a rectangular plate shape. Therefore, the container body 2 has a flat plate shape of which thickness direction is the Y-axis direction. As an example, the width of the container body 2 in the Z-axis direction is about 40 mm, the width of the container body 2 in the X-axis direction is about 30 mm, and the width of the container body 2 in the Y-axis direction is about 10 mm or less and preferably about 6 mm or less.

On a surface (a surface fixed to the second wall portion 12) of the first wall portion 11, a recess portion 11a and a notch portion 11b each having a flat bottom surface are formed. The recess portion 11a and the notch portion 11b are continuously formed. On a surface (a surface fixed to the first wall portion 11) of the second wall portion 12, a notch portion 12a having a flat bottom surface is formed. In the measurement container 1, the space inside the recess portion 11a forms the accommodation space 4, and the notch portion 11b and the notch portion 12a facing each other form the inlet 5. The inlet 5 is opened from one side (the upper side in FIGS. 1 to 3) in the Z-axis direction to the first region 4a. As an example, the width of the accommodation space 4 in the Z-axis direction is about 30 mm, the width of the accommodation space 4 in the X-axis direction is about 20 mm, and the width of the accommodation space 4 in the Y-axis direction is about 5 mm or less and preferably about 4 mm or less.

The wall portion 6 has a first inner surface 6a and a second inner surface 6b facing each other with the accommodation space 4 interposed therebetween in the Y-axis direction. In the measurement container 1, the first inner surface 6a is the bottom surface of the recess portion 11a of the first wall portion 11, and the second inner surface 6b is the surface of the second wall portion 12. The partitioning portion 7 is provided on the first inner surface 6a so that a gap (communication region) 13 is formed between the first inner surface 6a and the second inner surface 6b. The partitioning portion 7 is formed integrally with the first wall portion 11 by the same material as the first wall portion 11. In this manner, the partitioning portion 7 partitions the intermediate region 4c into one side S1 and the other side S2 so that the gap 13 which allows the one side S1 and the other side S2 to communicate with each other in the intermediate region 4c remains. As an example, the width of the gap 13 is about 1 mm or less.

The rotor 3 is arranged in the second region 4b. The rotor 3 is a rod-shaped member. As a specific example, the rotor 3 is configured by performing a plating process such as gold plating on a core formed of a magnetic material. As an example, the diameter of the rotor 3 is about 1 mm or less, and the length of the rotor 3 is about 10 mm or less. The support portion 8 which supports the rotor 3 is provided on the first inner surface 6a of the wall portion 6 (that is, the bottom surface of the recess portion 11a of the first wall portion 11) in the second region 4b. The support portion 8 is formed integrally with the first wall portion 11 by the same material as the first wall portion 11.

A surface 8a of the support portion 8 has a curved surface shape (for example, a partial shape of a spherical surface)

that is convex toward the accommodation space 4. Therefore, when a magnetic stirrer is operated outside the measurement container 1, the rotor 3 is rotated on the support portion 8 about an axis parallel to the Y-axis direction. Namely, the rotor 3 is rotated by the effect of magnetic force. The second region 4b where the rotor 3 is arranged has a shape corresponding to a rotation region of the rotor 3. More specifically, a third inner surface 6c (a side surface connecting the first inner surface 6a and the second inner surface 6b) of the wall portion 6 which defines the second region 4b has a shape of a portion of a cylindrical surface so that a constant gap is formed between the third inner surface 6c and the rotation region of the rotor 3. In addition, when the attractive magnetic force of the magnetic stirrer is not exerted outside the measurement container 1, the rotor 3 falls down on, for example, the third inner surface 6c of the wall portion 6.

Next, measurement examples using the measurement container 1 will be described. In the following measurement examples, the same sample containing whole blood is used, and myeloperoxidase activity and superoxide ($O_2-$) production activity are simultaneously measured. The activity of neutrophilic cells is evaluated on the basis of these measured data. In addition, the above-mentioned sample is, for example, a sample containing whole blood, and the above-mentioned characteristic is, for example, the activity of neutrophilic cells contained in the sample.

The neutrophilic cells are one type of white blood cells. The main role of neutrophilic cells is to phagocytize and sterilize bacteria and fungi that have entered a living body and to prevent infection. The neutrophilic cells form phagocytes that take the bacteria and the like inside neutrophils by wrapping the bacteria and the like with neutrophil plasma membranes. Next, the phagocytes fuse with granules, and contents of the granules are released into the phagocytes. Active oxygen (superoxide or hydrogen peroxide) is generated by an NADPH oxygenated oxygen system formed in the cell membrane (membrane of the phagocyte), and this active oxygen sterilizes the bacteria and the like. In addition, by the oxygen reaction of myeloperoxidase (EC number 1.11.2.2) contained in the contents of the granules, hypochlorous acid (HOCl) (or halogen equivalents thereof) from hydrogen peroxide ($H_2O_2$) and chlorine ions (Cl—) are produced, and the hypochlorous acid sterilizes bacteria and the like. Therefore, it is possible to evaluate the activity of neutrophilic cells by using the myeloperoxidase activity and the superoxide-production activity as indicators.

Figure 5:
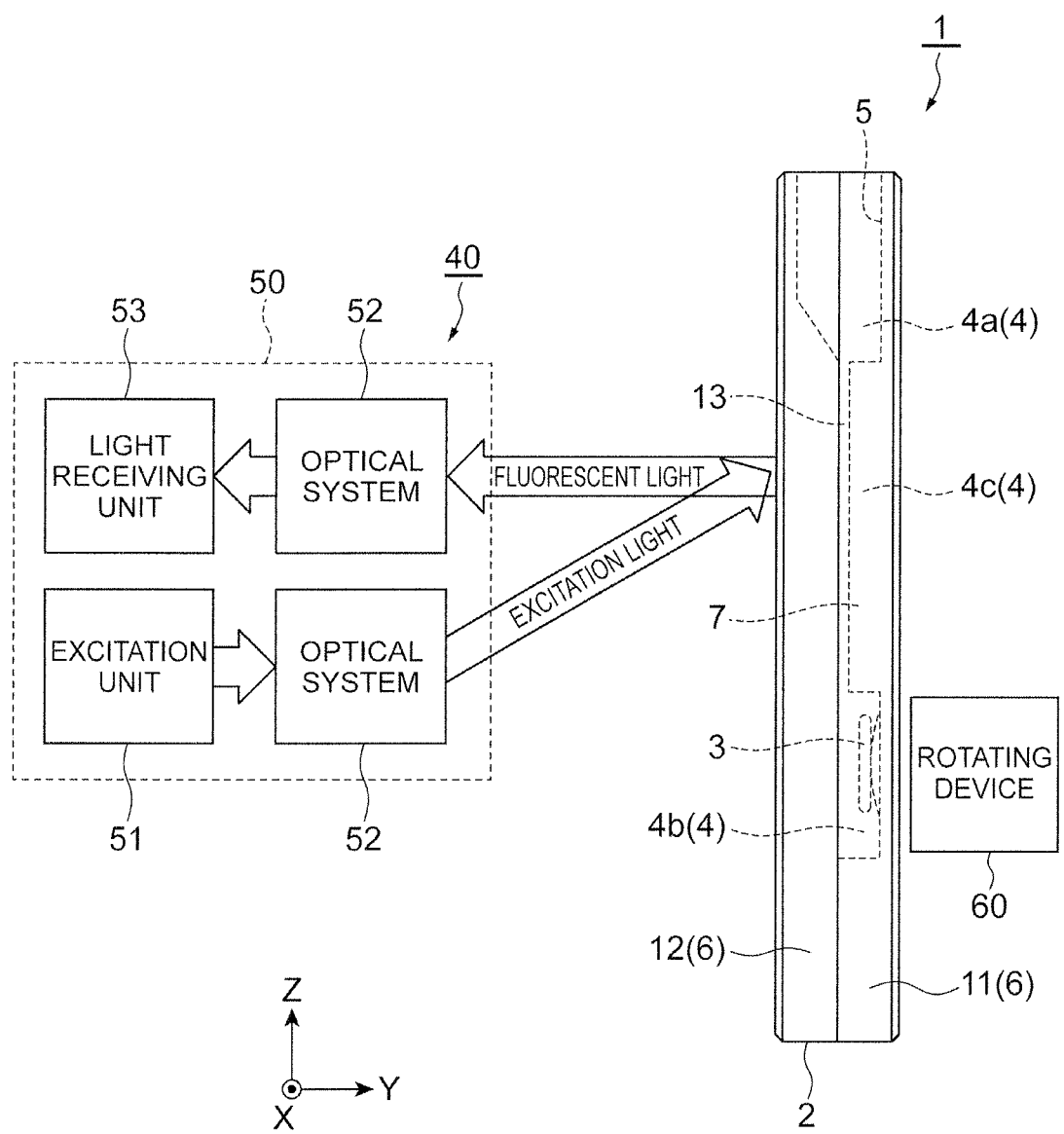
FIG. 5 is a side view of the measurement container of FIG. 1 in a state of being set in a measuring apparatus.

As illustrated in FIG. 5, a measuring apparatus 40 comprises an optical device 50 and a rotating device 60. The optical device 50 includes an excitation unit 51, a plurality of optical systems 52, and a light receiving unit 53. The excitation unit 51 has, for example, a light emitting element such as a laser diode or a light emitting diode. The excitation unit 51 irradiates the sample with excitation light through one optical system 52 to excite a fluorescent indicator or a chemiluminescent indicator contained in the sample and to generate fluorescent light from the fluorescent indicator or generate chemiluminescent light from the chemiluminescent indicator. The light receiving unit 53 has, for example, a light receiving element such as a photodiode converting light into an electric signal. The light receiving unit 53 detects the light generated in the sample through the other optical system 52. The light received by the light receiving unit 53 is the fluorescent light generated from the fluorescent indicator contained in the sample or the chemiluminescent light generated from the chemiluminescent indicator contained in the sample. Each optical system 52 is, for example, a lens that collects light.

The rotating device 60 is, for example, a magnetic stirrer that rotates the rotor 3 arranged in the measurement container 1.

The excitation unit 51 and the light receiving unit 53 are arranged on the same side with respect to the measurement container 1. The excitation unit 51 and the light receiving unit 53 are arranged, for example, on one side in the Y-axis direction with respect to the measurement container 1. This makes it easy to arrange the excitation unit 51, the light receiving unit 53, and the rotating device 60. In addition, similarly to the case of using a glass slide as a measurement container, the sample is irradiated with the excitation light on the same side with respect to the measurement container 1 to detect the fluorescent light obtained from the sample, and thus, it is possible to suppress the influence of light absorption by the sample, so that it is possible to perform more accurate measurement.

Figure 6:
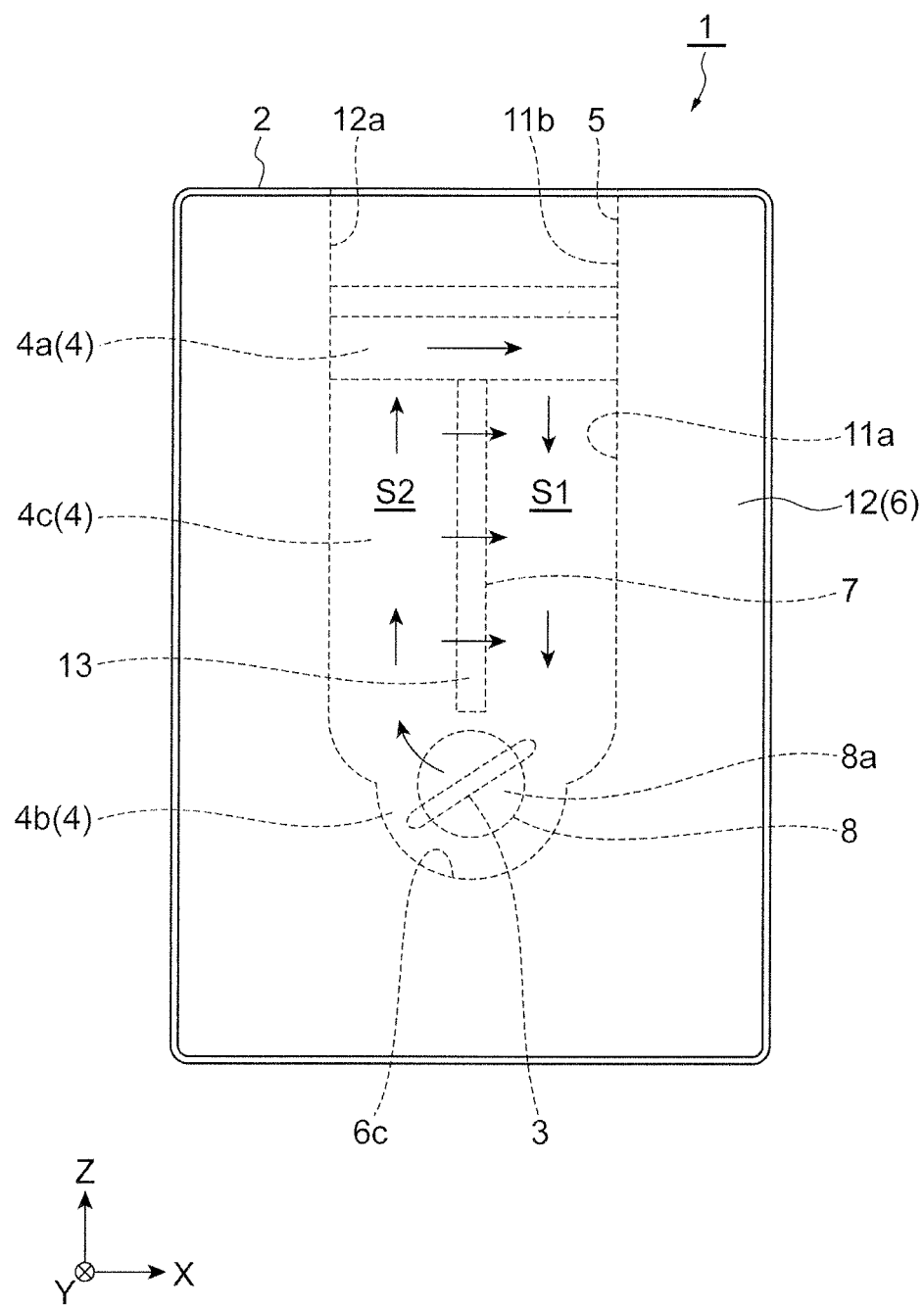
FIG. 6 is a front view of the measurement container of FIG. 1 in a state of being set in the measuring apparatus.

Next, the measurement examples using the measurement container 1 will be described in detail with reference to FIGS. 5 and 6. First, the measurement container 1 is set at a predetermined position of the measuring apparatus 40. For example, the measurement container 1 is set between the optical device 50 and the rotating device 60 in the Y-axis direction. Subsequently, by using a sample injection nozzle (not illustrated), a first solution (not illustrated) is introduced from the inlet 5 into the accommodation space 4. The first solution is, for example, a physiological saline solution, a buffer solution, or the like to which a fluorescent indicator and a chemiluminescent indicator are added. As the fluorescent indicator, aminophenyl fluorescein (APF) may be used. As the chemiluminescent indicator, 2-methyl-6-(4-methoxyphenyl)-3,7-dihydroimidazo [1,2-a] pyrazin-3-one (MCLA) may be used.

Subsequently, by using the sample injection nozzle, a second solution (not illustrated) is introduced from the inlet 5 into the accommodation space 4. The second solution is, for example, whole blood or the like. The "whole blood" means blood itself collected from a living body. A small amount (2 to 3 μL) of peripheral blood collected from a fingertip or the like by using a blood collecting device (for example, a lancet) used for measuring a daily blood sugar level by a diabetic patient may be used as the first sample. Because such a small amount of blood has little load, it is also possible to routinely evaluate the activity of neutrophilic cells. In addition, the first solution and the second solution may be introduced from the inlet 5 into the accommodation space 4 by using, for example, a pipette.

Subsequently, the rotor 3 is rotated from the outside of the container body 2 by the rotating device 60. As illustrated in FIG. 6, when the rotor 3 rotates, as viewed from the Y-axis direction, the first solution and the second solution introduced into the accommodation space 4 are mixed while flowing in the looping flow path from the first region 4a sequentially through the one side S1 of the intermediate region 4c, the second region 4b, and the other side S2 of the intermediate region 4c and returning to the first region 4a. In addition, the first solution and the second solution pass through the gap 13 and are mixed while flowing between the one side S1 and the other side S2 of the intermediate region 4c. Hereinafter, the mixture of the first solution and second solution is referred to as a sample.

Subsequently, the excitation unit 51 irradiates the sample with the excitation light through the optical system 52. When the fluorescent indicator APF reacts with HOCL, the fluorescent light having a wavelength of about 515 nm is generated by irradiation with excitation light having a wavelength of about 490 nm, so that the myeloperoxidase activity can be measured by detecting the fluorescent light having this wavelength. When the chemiluminescent indicator MCLA reacts with superoxide, the chemiluminescent light having a maximum emission wavelength of about 465 nm is generated, so that the superoxide-production activity can be measured by detecting the chemiluminescent light having this wavelength.

The sample accommodated in the measurement container 1 is intermittently irradiated with the excitation light from the excitation unit 51. The irradiation period and the non-irradiation period of the excitation light are repeated at a certain period. In the irradiation period of the excitation light, the fluorescent light and the chemiluminescent light generated in the sample are received by the light receiving unit 53, and an electric signal value V1 corresponding to the received light amount is obtained. In the non-irradiation period, the chemiluminescent light generated in the sample is received by the light receiving unit 53, and an electric signal value V2 corresponding to the received light amount is obtained. The fluorescent light intensity (that is, the measured value of myeloperoxidase activity) is obtained from the value obtained by subtracting the electric signal value V2 from the electric signal value V1. The chemiluminescent light intensity (that is, the measured value of superoxide-production activity) is obtained from the electric signal value V2. In this manner, both activities can be measured simultaneously under the same conditions, so that it is possible to more accurately evaluate the activity of neutrophilic cells.

During the measurement period, a stimulant is applied to the sample from, for example, a stimulant application nozzle (not illustrated). This stimulant may be any substance that activates a function (for example, migration and phagocytosis) of the neutrophilic cells. As a neutrophil stimulant, N-formyl-L-methionyl-L-leucyl-phenylalanine (fMLP), 4β-phorbol-12-myristate-13-acetate (PMA) and the like may be used. By adding a neutrophil stimulant to the sample, pseudo stimulation is given to the neutrophilic cells in the sample to induce an innate immune response (biological defense response), and thus, it is possible to evaluate the infection defense ability of the neutrophilic cells. On the contrary, in a case where the simulated stimulation is not given, it is possible to evaluate the state of the neutrophilic cells existing in the peripheral blood as it is. Therefore, it is possible to early evaluate the state (oxidative stress state) where the neutrophilic cells are excessively excited by, for example, vigorous exercise, smoking, or the like and, thus, active oxygen is released. Furthermore, it is also possible to evaluate the ability of inhibiting neutrophil over-activation (also referred to as antioxidant ability or oxidative stress prevention ability) caused by food and drink in vivo.

As described above, the measurement container 1 is configured to include the container body 2 where the first region 4a and the second region 4b located at both ends in the Z-axis direction and the intermediate region 4c located between the first region 4a and the second region 4b are continuously (serially) formed as the accommodation space 4 accommodating the sample and the inlet 5 through which the sample is introduced into the accommodation space 4 is formed and the rotor 3 which is arranged in the second region 4b and rotated by the effect of magnetic force, wherein the container body 2 includes the wall portion 6 which defines the accommodation space 4 and at least a portion of which has a light transmitting property and the partitioning portion 7 which partitions the intermediate region 4c into the one side S1 and the other side S2 in the X-axis direction perpendicular to the Z-axis direction, and wherein the partitioning portion 7 partitions the intermediate region 4c into the one side S1 and the other side S2 so that the gap 13 which allows the one side S1 and the other side S2 to communicate with each other in the intermediate region 4c remains.

In the measurement container 1, the partitioning portion 7 partitions the intermediate region 4c into one side S1 and the other side S2, and the rotor 3 is rotated by the effect of magnetic force in the second region 4b. Therefore, when a plurality of solutions are introduced, the plurality of solutions are mixed while the plurality of solutions flow in the looping flow path from the first region 4a sequentially through the one side S1 of the intermediate region 4c, the second region 4b, and the other side S2 of the intermediate region 4c and returning to the first region 4a. In addition, in the measurement container 1, the partitioning portion 7 partitions the intermediate region 4c into the one side S1 and the other side S2 so that the gap 13 which allows the one side S1 and the other side S2 to communicate with each other in the intermediate region 4c remains. Accordingly, flowing of the plurality of solutions and mixing of the plurality of solutions are facilitated. Therefore, according to the measurement container 1, when a plurality of solutions are introduced, it is possible to efficiently and uniformly mix the plurality of solutions.

Here, for example, when the sample containing whole blood is kept stationary during the measurement period, cells containing the neutrophilic cells contained in whole blood are slowly precipitated in the direction of gravity, and the concentration of cells in the direction of gravity is changed. In addition, when the sample is kept stationary during the measurement period, the red blood cells may aggregate, and thus, irregularity in light transmittance may occur. Therefore, when the sample is kept stationary during the measurement period, the measurement result may be inaccurate. On the contrary, in the embodiment, a plurality of solutions contained in the measurement container 1 are stirred by rotation of the rotor 3 subsequently even after sufficient mixing, so that the precipitation and aggregation of the neutrophilic cells are suppressed. Therefore, the neutrophilic cells are homogenized in the accommodation space 4, so that the measurement result is suppressed from being inaccurate.

Next, the effects in the case of employing the measurement container 1 as a measurement container will be described in comparison with the case of employing a glass slide as a measurement container. In the measurement container 1, the sample is accommodated in the accommodation space 4 formed in the container body 2. For this reason, for example, in comparison with the case of using a glass slide as a measurement container, the sample is hard to evaporate. Therefore, the measurement result is suppressed from being inaccurate due to a change in liquid amount of the sample. In addition, in the measurement container 1, the sample is stirred by the rotor 3 arranged in the accommodation space 4. For this reason, for example, in comparison with a case where the sample is stirred with air injected from an injector after mounting the sample on the glass slide, unstable measurement results due to turbulence of the liquid surface of the sample are suppressed. In addition, in the measurement container 1, for example, in comparison with the case of employing a glass slide as a measurement container, a humidifying device for preventing evaporation of the sample is unnecessary, so that the apparatus can be miniaturized. In addition, because the stirring of the sample by the air injected from the injector becomes unnecessary, the decrease in temperature caused by the heat of vaporization is suppressed, so that the temperature stability of the sample is improved. In addition, because the injector may be omitted, the whole device may be inexpensive. In addition, because the exposure of the sample is reduced, it is advantageous for hygiene, and operability is improved. In addition, because the adsorption of the sample to the measurement unit around the measurement container 1 caused by the evaporation of the sample or the like is reduced, the stability of the signal is improved.

In addition, in the measurement container 1, the container body 2 has a shape of a flat plate of which thickness direction is the Y-axis direction perpendicular to the Z-axis direction and the X-axis direction. Accordingly, because the thickness (the thickness in the Y-axis direction) of the above-described looping flow path is reduced, when a plurality of solutions are introduced, it is possible to more efficiently and more uniformly mix the plurality of solutions. In addition, because the thickness (the thickness in the Y-axis direction) of the accommodation space 4 is reduced, it is possible to efficiently irradiate the sample accommodated in the accommodation space 4 with light, and the influence of light absorption of a blood sample on the measurement accuracy is minimized, so that it is possible to efficiently collect the light emitted from the sample.

In addition, in the measurement container 1, the wall portion 6 has the first wall portion 11 and the second wall portion 12 that face each other and are fixed to each other in the Y-axis direction, and the accommodation space 4 includes a space inside the recess portion 11*a* which is formed at least in the first wall portion 11. Accordingly, it is possible to easily and reliably form the accommodation space 4 where the partitioning portion 7 is arranged.

In addition, in the measurement container 1, the wall portion 6 has the first inner surface 6*a* and the second inner surface 6*b* that face each other with the accommodation space 4 interposed therebetween in the Y-axis direction, and the partitioning portion 7 is provided on the first inner surface 6*a* so that the gap 13 as a communication region is formed between the first inner surface 6*a* and the second inner surface 6*b*. Accordingly, it is possible to easily and reliably form the partitioning portion 7 that partitions the intermediate region 4*c* while leaving the gap 13.

In addition, in the measurement container 1, the rotor 3 is rotated about an axis parallel to the Y-axis direction, and the second region 4*b* has a shape corresponding to the rotation region of the rotor 3. Accordingly, it is possible to more efficiently flow the solution in the above-described looping flow path.

In addition, in the measurement container 1, the rotor 3 is a rod-shaped member, the container body 2 further has the support portion 8 which supports the rotor 3 in the second region 4*b*, and the surface 8*a* of the support portion 8 has a curved surface shape that is convex from the wall portion 6 toward the accommodation space 4. Accordingly, it is possible to efficiently and stably rotate the rotor 3 by, for example, a magnetic stirrer. In addition, because the surface 8*a* of the support portion 8 which supports the rotor 3 has a curved surface shape, it is possible to facilitate positioning of the rotor 3 when the rotor 3 is rotated by, for example, a magnetic stirrer. In addition, in comparison with a case where the support portion 8 is not provided, because the contact area between the rotor 3 and the portion which supports the rotor 3 is reduced, the rotational resistance of the rotor 3 can be suppressed, and it is possible to suppress the cells contained in the sample from being damaged at the portion where the rotor 3 and the portion which supports the rotor 3 slide.

In addition, in the measurement container 1, the inlet 5 is opened to the first region 4*a*. Accordingly, in comparison with a case where the inlet 5 is opened to the second region 4*b* or the intermediate region 4*c*, restriction on the layout can be suppressed. Specifically, for example, in a case where the inlet 5 is opened to the second region 4*b*, the inlet cannot be opened at least in the direction facing the rotating device 60. For example, in a case where the inlet 5 is opened to the intermediate region 4*c*, the inlet cannot be opened at least in the direction of the one side in the Z-axis direction of the intermediate region 4*c*. On the contrary, because the inlet 5 is opened to the first region 4*a*, the inlet 5 can also be opened in the direction opposite to the rotating device 60, and the inlet 5 can also be opened in the direction of the one side in the Z-axis direction of the first region 4*a*. Therefore, because the measurement container 1 can be arranged in various directions with respect to peripheral devices, restriction on the layout can be suppressed.

The measurement container 1 is configured to include the container body 2 where the first region 4*a* and the second region 4*b* located at both ends in the Z-axis direction and the intermediate region 4*c* located between the first region 4*a* and the second region 4*b* are continuously formed as the accommodation space 4 accommodating the sample and the inlet 5 through which the sample is introduced into the accommodation space 4 is formed, wherein the container body 2 includes the wall portion 6 which defines the accommodation space 4 and at least a portion of which has a light transmitting property and the partitioning portion 7 which partitions the intermediate region 4*c* into the one side S1 and the other side S2 in the X-axis direction perpendicular to the Z-axis direction, wherein the second region 4*b* is a region where the rotor 3 to be rotated by the effect of magnetic force is arranged, and wherein the partitioning portion 7 partitions the intermediate region 4*c* into the one side S1 and the other side S2 so that the gap 13 which allows the one side S1 and the other side S2 to communicate with each other in the intermediate region 4*c* remains.

According to the measurement container 1, for the above-mentioned reasons, when a plurality of solutions are introduced, it is possible to efficiently and uniformly mix the plurality of solutions.

In addition, in the measurement container 1, because the rotor 3 is arranged in the second region 4*b*, formation of vortexes in the intermediate region 4*c* is suppressed. Therefore, for example, in the case of measuring the characteristics of the sample by irradiating the intermediate region 4*c* with the excitation light, it is possible to prevent the measurement result from being inaccurate.

In addition, in the measurement container 1, when viewed from the inlet 5, the outer edge of the inlet 5 includes the outer edge of the accommodation space 4. Accordingly, when the sample is introduced from the inlet 5, the sample adheres to the inner wall surface which defines the accommodation space 4, so that it is possible to prevent the measurement accuracy from being deteriorated. In addition, it is possible to simultaneously introduce a plurality of the samples from the inlet 5.

In addition, in the measurement container 1, because the surface of the rotor 3 is plated with gold, it is possible to suppress a chemical reaction between the rotor 3 and the sample. In addition, because the rotor 3 is formed by plating a core formed of a magnetic material with gold or the like, it is possible to achieve inexpensive, disposable products.

Heretofore, although one embodiment of the present disclosure has been described above, the present disclosure is not limited to the above-described embodiment.

Figure 7:
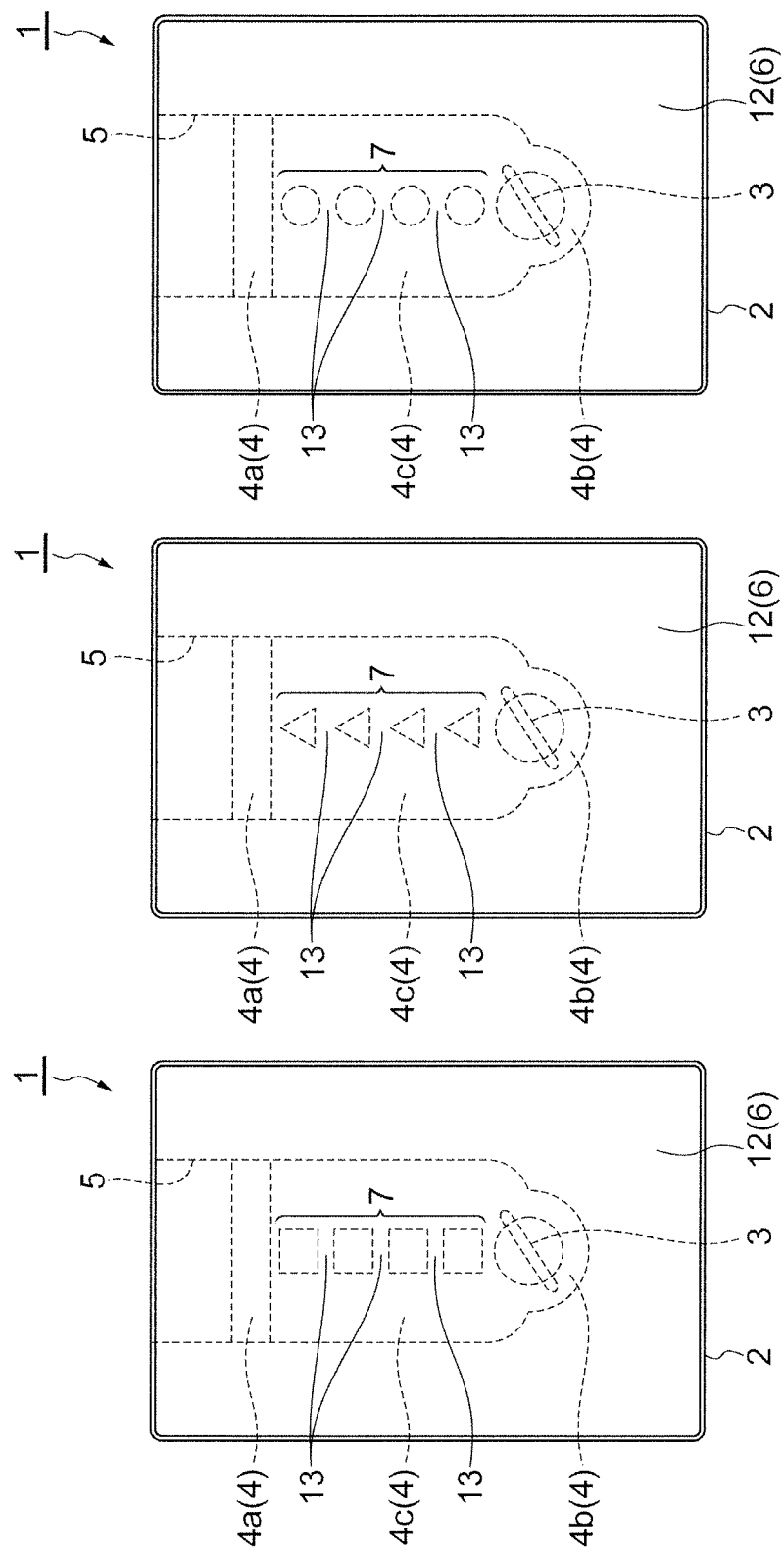
FIG. 7A is a front view of a measurement container according to Modified Example 1.
FIG. 7B is a front view of a measurement container according to Modified Example 2.
FIG. 7C is a front view of a measurement container according to Modified Example 3.

The partitioning portion 7 is not limited to the example described above. As illustrated in FIGS. 7A, 7B, and 7C, the partitioning portion 7 may be configured with a plurality of rods that extend along the Z-axis direction and are separated from each other. In this case, the region between the plurality of rods forms the gap 13. The cross-sectional shape of each rod may be various shapes such as a quadrangular shape, a triangular shape, or a circular shape. In addition, in this case, each rod may be formed on any one of the first inner surface 6a and the second inner surface 6b or may be formed on both of the first inner surface 6a and the second inner surface 6b. In addition, as long as the gap 13 which allows the one side S1 and the other side S2 to communicate with each other in the intermediate region 4c can be left, the partitioning portion 7 may be formed on, for example, both of the first inner surface 6a and the second inner surface 6b. In this case, the gap 13 is formed in the partitioning portion 7.

Figure 8:
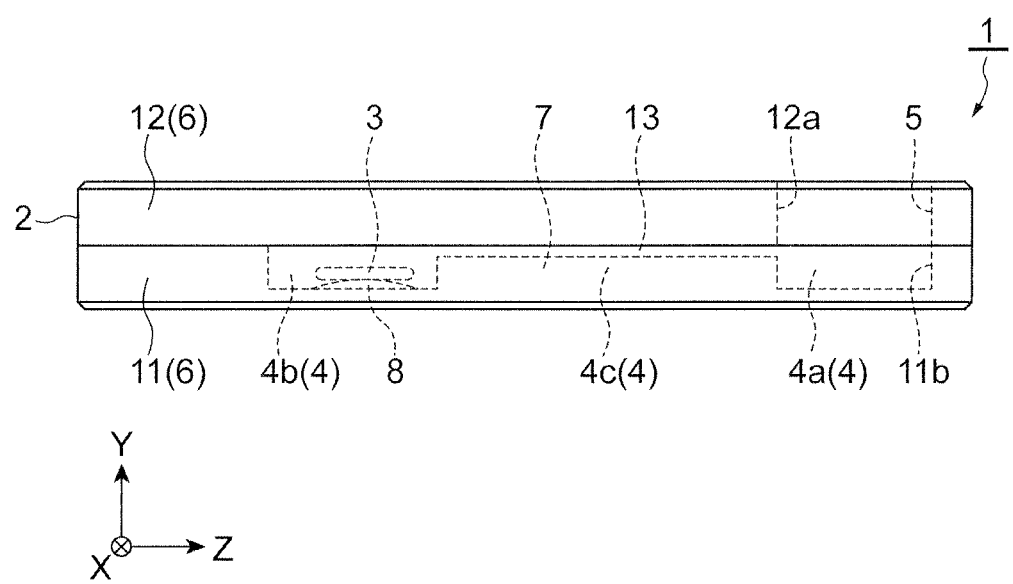
FIG. 8 is a side view of a measurement container according to Modified Example 4.
Figure 9:
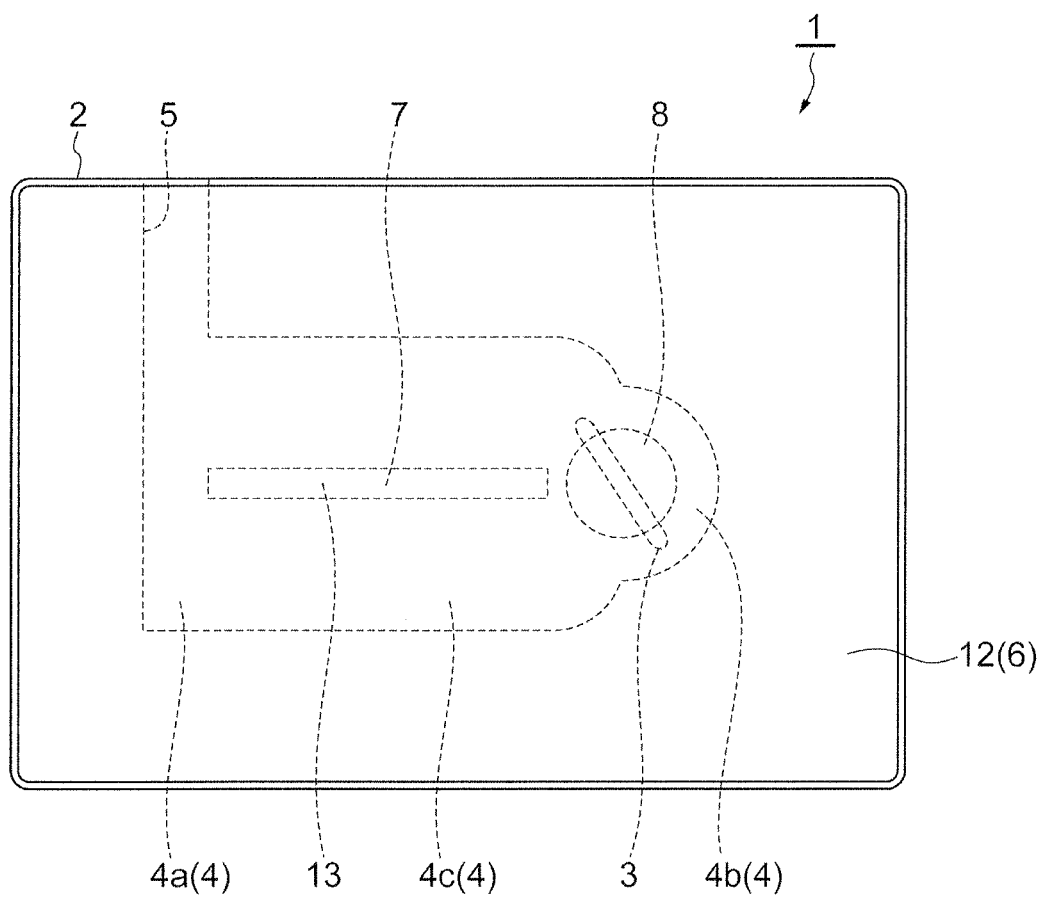
FIG. 9 is a front view of a measurement container according to Modified Example 5.

In addition, the inlet 5 is not limited to the example described above. As illustrated in FIG. 8, the inlet 5 may be opened to the one side in the Y-axis direction (the third direction perpendicular to the first direction and the second direction). As illustrated in FIG. 9, the inlet 5 may be opened to the one side in the X-axis direction (the second direction perpendicular to the first direction). In this manner, the inlet 5 may be opened in various directions. In addition, as long as the sample can be introduced into the accommodation space 4, the position where the inlet 5 is formed is not limited. The inlet 5 may be formed in, for example, the second region 4b or the intermediate region 4c.

In addition to the space inside the recess portion 11a formed in the first wall portion 11, the accommodation space 4 may include a recess portion formed in the second wall portion 12. For example, in addition to the first wall portion 11 and the second wall portion 12, the container body 2 may have a side wall portion, and the accommodation space S may be defined by the first wall portion 11, the second wall portion 12, and the side wall portion. In addition, the container body 2 may have, for example, a cylindrical shape.

In addition, although the example where the wall portion 6 is made of a material having a light transmitting property, it is not limited thereto. Only a portion (for example, a portion corresponding to the intermediate region 4c) of the wall portion 6 which defines the accommodation space 4 may have a light transmitting property. In this case, the sample is irradiated with the excitation light through the portion of the wall portion 6 having a light transmitting property.

In addition, the dimensions of the measurement container 1 are not limited. The dimensions of the measurement container 1 can be appropriately set depending on the use environment and the requirements.

In addition, as long as the measurement container 1 has a region where the rotor 3 rotated by the effect of magnetic force is arranged, the rotor 3 may not be provided.

The measuring apparatus and the measurement container described above can be used in various situations. For example, not only in agriculture, forestry and fishery industry, and food manufacturing industry such as functional food field, breeding science of breeding improvement and the like, livestock management, and development of unused resources but also as tools for management of human health condition and selection of appropriate food, the measuring apparatus and the measurement container described above can be used in a wide range of fields such as hospital and examination institution. In addition, the measuring apparatus and the measurement container described above can be used as an inexpensive, simple function evaluation tool for a human test. In addition, the measuring apparatus and the measurement container described above are expected to be generally widely spread in terms of simplicity that cumbersome operations and specialized techniques are not required.

What is claimed is:

1. A measurement container comprising:
   a container body where a first region and a second region located at both ends in a first direction and an intermediate region located between the first region and the second region are continuously formed as an accommodation space accommodating a sample and an inlet through which the sample is introduced into the accommodation space is formed; and
   a rotor which is arranged in the second region and rotated by an effect of magnetic force,
   wherein the container body includes:
   a wall portion which defines the accommodation space and at least a portion of which has a light transmitting property; and
   a partitioning portion which partitions the intermediate region into one side and the other side in a second direction perpendicular to the first direction,
   wherein the partitioning portion partitions the intermediate region into the one side and the other side so that a communication region which allows the one side and the other side to communicate with each other in the intermediate region remains,
   wherein the container body is configured such that a looping flow path from the first region sequentially through the one side of the intermediate region, the second region, and the other side of the intermediate region and returning to the first region is formed by the rotation of the rotor, and
   wherein the second region is entirely delimited by the wall portion and the intermediate region such that the second region is closed except at the intermediate region.

2. The measurement container according to claim 1, wherein the container body has a shape of a flat plate of which thickness direction is a third direction perpendicular to the first direction and the second direction.

3. The measurement container according to claim 1, wherein the wall portion has a first wall portion and a second wall portion that face each other and are fixed to each other in a third direction perpendicular to the first direction and the second direction, and
   wherein the accommodation space includes at least a space inside a recess portion formed in the first wall portion.

4. The measurement container according to claim 1, wherein the wall portion has a first inner surface and a second inner surface that face each other with the accommodation space interposed therebetween in a third direction perpendicular to the first direction and the second direction, and
   wherein the partitioning portion is provided on the first inner surface so that a gap as the communication region is formed between the partitioning portion and the second inner surface.

5. The measurement container according to claim 1, wherein the rotor is rotated about an axis parallel to a third direction perpendicular to the first direction and the second direction, and
   wherein the second region has a shape corresponding to a rotation region of the rotor.

6. The measurement container according to claim 1, wherein the rotor is a rod-shaped member,
wherein the container body further includes a support portion which supports the rotor in the second region, and
wherein a surface of the support portion has a curved surface shape which is convex toward the accommodation space.

7. The measurement container according to claim 1, wherein the inlet is opened to the first region.

8. A measurement container comprising:
a container body where a first region and a second region located at both ends in a first direction and an intermediate region located between the first region and the second region are continuously formed as an accommodation space accommodating a sample and an inlet through which the sample is introduced into the accommodation space is formed,
wherein the container body includes:
a wall portion which defines the accommodation space and at least a portion of which has a light transmitting property; and
a partitioning portion which partitions the intermediate region into one side and the other side in a second direction perpendicular to the first direction,
wherein the second region is a region where a rotor to be rotated by an effect of magnetic force is arranged,
wherein the partitioning portion partitions the intermediate region into the one side and the other side so that a communication region which allows the one side and the other side to communicate with each other in the intermediate region remains,
wherein the container body is configured such that a looping flow path from the first region sequentially through the one side of the intermediate region, the second region, and the other side of the intermediate region and returning to the first region is formed by the rotation of the rotor, and
wherein the second region is entirely delimited by the wall portion and the intermediate region such that the second region is closed except at the intermediate region.

* * * * *